United States Patent [19]

Kim et al.

[11] Patent Number: 5,645,596
[45] Date of Patent: Jul. 8, 1997

[54] CERAMIC VERTEBRAE PROSTHESIS

[75] Inventors: Phyo Kim; Masao Suzuki, both of Tokyo, Japan

[73] Assignee: Asahi Kogaku Kogyo Kabushiki Kaisha, Tokyo, Japan

[21] Appl. No.: 268,103

[22] Filed: Jul. 6, 1994

[30] Foreign Application Priority Data

Jul. 7, 1993 [JP] Japan ................... 5-037185
Nov. 12, 1993 [JP] Japan ................... 5-060953

[51] Int. Cl.$^6$ ................................... A61F 2/44
[52] U.S. Cl. ................................................ 623/17
[58] Field of Search ........................ 623/1, 11, 16, 623/17, 18; 606/60–63

[56] References Cited

U.S. PATENT DOCUMENTS

| | | | |
|---|---|---|---|
| 3,867,728 | 2/1975 | Stubson et al. | 623/17 |
| 4,713,076 | 12/1987 | Draenert | 623/23 |
| 4,759,766 | 7/1988 | Buetiner-Janz et al. | 623/17 |
| 4,798,585 | 1/1989 | Inoue et al. | |
| 4,863,477 | 9/1989 | Monson | 623/17 |
| 4,946,378 | 8/1990 | Hirayama et al. | |
| 4,969,913 | 11/1990 | Ojima | |
| 5,017,518 | 5/1991 | Hirayama et al. | |
| 5,030,611 | 7/1991 | Ogawa et al. | |
| 5,064,436 | 11/1991 | Ogiso et al. | |
| 5,082,803 | 1/1992 | Sumita | |
| 5,123,926 | 6/1992 | Pisharodi | 623/17 |
| 5,137,534 | 8/1992 | Sumita | |
| 5,147,361 | 9/1992 | Ojima et al. | |
| 5,158,756 | 10/1992 | Ogawa et al. | |
| 5,171,720 | 12/1992 | Kawakami | |
| 5,215,941 | 6/1993 | Yasukawa | |
| 5,306,307 | 4/1994 | Senter et al. | 623/17 |
| 5,306,309 | 4/1994 | Wagner et al. | 623/17 |
| 5,314,478 | 5/1994 | Oka et al. | 623/18 |

Primary Examiner—Robert A. H. Clarke
Attorney, Agent, or Firm—Greenblum & Bernstein, P.L.C.

[57] ABSTRACT

A ceramic vertebrae prosthesis to be inserted in a cavity defined between upper and lower vertebra bodies with a removed intervertebral disk or disks is provided with upper and lower convex contact surfaces that come into contact with the upper and lower vertebra bodies.

21 Claims, 5 Drawing Sheets

CERAMIC VERTEBRAE PROSTHESIS

BACKGROUND OF THE INVENTION

1. Field of the Invention

The present invention relates to a ceramic vertebrae prosthesis which utilized as a substitute for one or more intervertebral disks that have been resected in a resection operation.

2. Description of the Related Art

If a nerve root is subject to a pressure due to an injury of an intervertebral disk, such as a cervical vertebrae, various neurological symptoms often arise therefrom. To cure this problem, the injured portion is usually subject to local rest and fixation thereof and a conservative curing process, such as an extensive curing process. Notwithstanding, if pain is not remitted, or the injury is too severe to be restored by such a curing procedure, a patient undergoes a surgical operation. There are two surgical operation methods in which the injured intervertebral disk is removed in front of the body of the vertebra or the vertebral arch is partly resected in the rear of the body of the vertebra so as to deliver a hernia. The first operation method in which the injured intervertebral disk is resected in front of the body of the vertebra is referred to as a forward adhesion in which a bone is implanted and adhered in a cavity formed between the upper and lower bodies of vertebra.

In such a forward adhesion, in many cases, a self-iliac bone is used as a bone to be implanted. However, a patient suffers from heavy burden and physical load as a result of to a secondary invasive procedure necessitates by the extraction of the iliac bone. To this end, prostheses, such as ceramics have been recently used and implanted instead of the self-iliac bone. In general, the ceramics are stable in and highly biocompatible, with the organ in which the prosthesis is to be grafted.

However, the ceramics are brittle and hard, and accordingly are weak with respect to physical shock. It is necessary for a vertebra prosthesis to have a mechanical strength strong enough to resist the compression load exerted to upper and lower vertebra bodies. In addition thereto, the vertebra prosthesis must be brought into direct contact with or directly adhered to the bone without an intervening soft tissue between the prosthesis and the bone while no bone resorption occurs between the upper and lower vertebra bodies.

The shape of the prosthesis is such that the portion of the bone to be resected is as small as possible, since the prosthesis must be partly removed in accordance with the shape of the vertebrae prosthesis. In general, a known prosthesis (prosthesis other than ceramics) is subject to a certain stress (pressure) due to repeated absorption and bone resorption with respect to a sound bone to keep a balanced state. However in particular, the ceramic cervical vertebrae prosthesis in which no bone resorption takes place must be shaped so as to disperse or uniformly distributes the compression stress. Nevertheless, the conventional ceramic vertebrae prosthesis has been focused mainly on the strength of the material of which the vertebrae prosthesis is made, to increase the resistance to the compression load but little or no consideration of the shape have been taken into account. Moreover, little or no attempts to reduce the amount of the bone to be resected have been made.

Furthermore, it is necessary to expand the distance between the upper and lower vertebra bodies so as to insert the vertebrae prosthesis therebetween. However, the conventional vertebrae prosthesis cannot, by itself, expand the distance between the upper and lower vertebra bodies. Accordingly, it is necessary to use a special expanding tool or device, thus resulting in an increase in the time for the operation. In particular, a conventional elongated prosthesis, which is to be inserted to substitute for a plurality of removed vertebra bodies, is usually in the form of a circular or angular post linearly extending in the vertical direction. Accordingly, it does not conform to the profile of the continuously curved vertebra bodies. Consequently, the conventional elongated prostheses were morphologically unnatural.

SUMMARY OF THE INVENTION

The primary object of the present invention is to provide an improved prosthesis having an increased resistance to the compression stress, wherein no bone resorption occurs; the amount of the vertebra body to be resected upon operation can be minimized; the prosthesis can be easily inserted; and, the inserted prosthesis is stably held in the inserted position.

Another object of the present invention is to provide an improved ceramic prosthesis for a plurality of vertebra bodies having a morphologically natural shape.

These and other objects of the present invention will be appreciated more fully after the following descriptions concerning preferred embodiments of the present invention.

One of the most significant features of the present invention is addressed to the shape of the ceramic vertebrae prosthesis. Namely, the inventors have found that the contact surface of the vertebra body with the intervertebral disk is macroscopically a concave surface. Consequently, if the vertebrae prosthesis, which substitutes for the intervertebral disk, is provided with a convex surface corresponding to the concave contact surface, technical advantages can be achieved. Particularly an increase in resistance to achieved compression load, the prevention of a bone resorption, a minimization of the amount of vertebral bone to be resected, ease of insertion, and an increase in stableness after insertion, etc., can be all achieved.

Namely, according to an aspect of the present invention, there is provided a ceramic vertebrae prosthesis to be inserted in a cavity defined between upper and lower vertebra bodies, by removal of an intervertebral disk or disks, wherein the vertebrae prosthesis is provided with upper and lower outwardly convex contact surfaces that come into contact with the upper and lower vertebra bodies.

The outwardly convex contact surfaces of the vertebrae prosthesis provide an increased resistance to the compression stress exerted by the upper and lower vertebra bodies. Since the contact surfaces of the vertebra bodies that come into contact with the prosthesis are macroscopically concave surfaces, the amount of bone of the vertebra bodies to be resected, depending on the convex surfaces of the prosthesis, can be minimized. The engagement of the concave contact surfaces of the vertebra bodies and the convex contact surfaces of the prosthesis provides a high resistance to the compression stress not only in the vertical direction (longitudinal direction of the vertebrae) but also in the lateral direction slightly deviated from the longitudinal direction, since the stress is substantially uniformly distributed or dispersed. The distribution of the stress prevents the bone of the vertebrae from being resorbed by the prosthesis, that is, no bone resorption takes place. Consequently, no sinking of the prosthesis results, so that the prosthesis appropriately and stably functions as a substitute for the removed vertebrae for a long time, without causing a deformation of the remaining vertebrae.

The contact surfaces of the prosthesis with the vertebrae can be made of either a single curvature of or a composite curved surface consisting of different curvatures of curved surfaces in combination. For instance, in the composite curved surface, the curvature thereof in a section perpendicular to the insertion direction of the prosthesis is different from the curvature in a section parallel with the insertion direction.

Preferably, the width of the prosthesis gradually decreases toward the front end thereof as viewed in the insertion direction thereof, so that the prosthesis can be easily inserted in a cavity or space between the upper and lower vertebra bodies. Namely, for ease for insertion of the prosthesis, the latter is preferably of a wedge-shape. Meanwhile, it should be recalled that the prosthesis is preferably provided with curved surfaces as a whole, as mentioned above. In view of these two different requirements, it is preferable that each of the curved contact surfaces of the prosthesis in a cross section parallel with the insertion direction thereof is made up of a front curved surface having a small curvature and a rear curved surface opposite thereto having a large curvature, so as to satisfy the two requirements.

Another feature of the present invention is directed to an improved cervical prosthesis. The cervical vertebrae are in the form of a forwardly convex arch. Accordingly, the cervical prosthesis, to substitute for the cervical vertebrae, should be correspondingly curved into an arch-shape so as to provide a morphologically natural form. Furthermore, if the upper and lower contact surfaces of the cervical prosthesis, with the upper and lower vertebra bodies, are made of convex surfaces, the compression stress can be effectively dispersed or distributed.

Namely, according to another aspect of the present invention, there is provided a ceramic cervical vertebrae prosthesis for a multiple vertebra bodies to be inserted in a cavity formed by resecting a plurality of continuous cervical vertebrae, wherein the vertebrae prosthesis is provided with an outwardly arched front surface, corresponding to front surfaces of the removed vertebra bodies, and upper and lower convex contact surfaces that come into contact with the corresponding upper and lower vertebra bodies.

In the present invention, there is no limitation on the radius of curvature of the front surface of the ceramic cervical vertebrae prosthesis, but preferably, the radius of curvature is 100 mm to 200 mm. The radius of curvature of the rear surface of the ceramic cervical vertebrae prosthesis can be the same as or different from that of the front surface thereof. If the radius of curvature of the rear surface of the ceramic cervical vertebrae prosthesis is smaller than the radius of curvature of the front surface thereof, the ceramic cervical vertebrae prosthesis can be easily and advantageously inserted from the front of the vertebrae.

If the upper and lower contact surfaces of the cervical vertebrae prosthesis are made of outwardly convex surfaces, the resistance to the compression stress exerted by the upper and lower vertebra bodies, can be increased. Since the contact surfaces of the vertebra bodies that come into contact with the prosthesis are macroscopically concave surfaces, the amount of bone of the vertebra bodies to be resected, depending on the convex surfaces of the prosthesis, can be minimized. The engagement of the concave contact surfaces of the vertebra bodies and the convex contact surfaces of the prosthesis provides a high resistance to the compression stress not only in the vertical direction (i.e., direction connecting the two adjacent vertebrae bodies) but also in the lateral direction slightly deviated from the longitudinal direction, since the stress is substantially uniformly distributed or dispersed. The distribution of the stress prevents the bone of the vertebrae from being resorbed by the prosthesis, that is, no bone resorption takes place. Consequently, no sinking of the prosthesis is caused, so that the prosthesis appropriately and stably functions as a substitute for the removed vertebrae for long time without causing a deformation of the remaining vertebrae.

The contact surfaces of the prosthesis with the vertebrae can be made of either a single curvature or a composite curved surface consisting of different curvatures of curved surfaces in combination. For instance, in the composite curved surface, the curvature thereof in a section perpendicular to the insertion direction of the prosthesis is different from the curvature in a section parallel with the insertion direction.

The ceramic of which the vertebrae prosthesis (including the cervical vertebrae prosthesis) is made can be selected from alumina, zirconia, or calcium phosphate ceramic, etc. Among them, in particular, the calcium phosphate ceramic is advantageous and preferable since a spontaneous adhesion of the calcium phosphate ceramic vertebrae prosthesis to the associated vertebrae takes place, resulting in a firm connection therebetween. As the calcium phosphate ceramic calcium phosphate compound whose Ca/P ratio is 1.0 to 2.0, such as hydroxyapatite, tricalcium phosphate, tetracalcium phosphate, calcium hydrogen phosphate, can be advantageously used. These substances can be used singly or as a mixture or compound.

More preferably, the vertebrae prosthesis of the present invention is made of porous calcium phosphate ceramics whose porosity (true porosity) is 20 to 55%, and preferably 30 to 45%. In case of porous ceramics, an accelerated adhesion thereof to the vertebra bodies can be expected owing to the penetration of the osteoblast into the pores at the contact surface of the vertebrae prosthesis and the vertebra bodies. This expedites the recovery of function of the vertebrae. If the (true) porosity is below 20%, the number of the pores is too small to expect the above-mentioned advantages. Conversely, if the porosity is above 55%, the mechanical strength of the prosthesis is too small to resist the compression stress. The (true) porosity refers to a percentage of a total volume of the closed pores (cells) and the open pores (cells) to a unit volume.

The ceramic vertebrae prosthesis can be produced as follows. In the following discussion, hydroxyapatite ceramics are used to make the ceramic vertebrae prosthesis by way of example.

Phosphate salt and calcium salt are synthesized in a wet composition process per se known to obtain a hydroxyapatite slurry. The slurry thus obtained is dried by use of a rotary drum type drier or the like to obtain a hydroxyapatite powder. The powder is pressed, for example, by use of a dry type static hydraulic press into the shape of the ceramic vertebrae prosthesis. The compact member thus obtained is heated at 1000° C. to 1200° C. in an electric furnace to obtain vertebrae prostheses (including cervical vertebrae prostheses). Alternatively, it is possible to employ a slurry casting process, an injection molding process, or to produce a green compact member which is machined by a lathe into a predetermined shape.

The methods mentioned above are useful in producing a dense vertebrae prosthesis whose porosity is less than 10%.

To produce a porous vertebrae prosthesis whose porosity is more than 20%, a foaming agent and water are added to and mixed with the hydroxyapatite powder to obtain a foamed slurry which is then dried. The dried slurry is machined by a milling machine or the like into a predetermined shape of vertebrae prosthesis which is thereafter heated at 1000° to 1200° C. in an electric furnace to obtain a final product, i.e., a vertebrae prosthesis. In the process mentioned above, it is alternatively possible to add a powder of thermally disappearing substance, so that the mixture is formed and heated to produce a vertebrae prothesis. A thermally disappearing substance refers to any of various plastic or wood powders that disintegrate when heated at high temperatures, Furthermore, the vertebrae prosthesis according to the present invention can be made of ceramics having a dense center portion and a porous circumferential portion. The dense center portion mainly contributes to an increase in the mechanical strength as a whole, and the porous circumferential portion mainly contributes to an accelerated adhesion of the vertebrae prosthesis to the vertebra bodies. To produce such a ceramic vertebrae prosthesis having a dense center portion and a porous circumferential portion, for example, a dried dense material corresponding to the center portion is fitted in a dried porous material corresponding to the circumferential portion and the assembly is heated, or the dried dense material is adhered to the dried porous material by an apatite slurry and the assembly is heated.

The subject of the present invention is directed to a structure or shape of a vertebrae prosthesis and not to the production process thereof. Accordingly, the manufacturing process is not limited to those mentioned above.

The present disclosure relates to subject matter contained in Japanese utility model application Nos. 5-37185 (filed on Jul. 7, 1993) and 5-60953 (filed on Nov. 12, 1993) which are expressly incorporated herein by reference in their entirety.

BRIEF DESCRIPTION OF THE DRAWINGS

The present invention will be described below in detail with reference to the accompanying drawings, in which.

DESCRIPTION OF THE PREFERRED EMBODIMENTS

Figure 1:
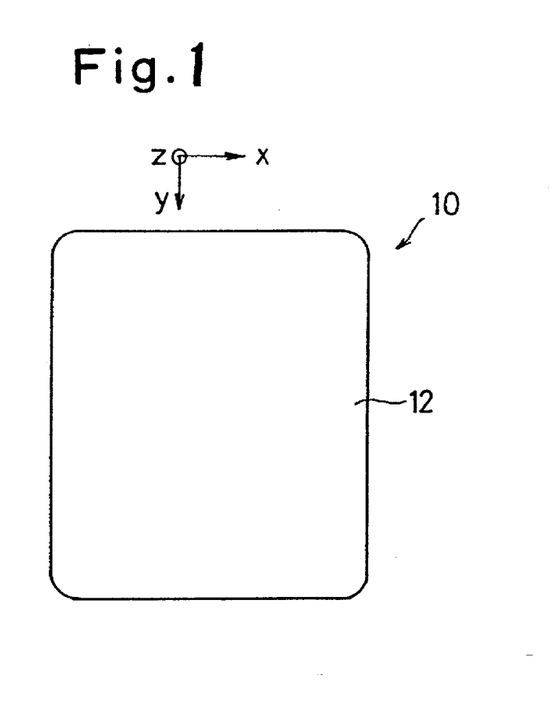
FIG. 1 is a plan view of a ceramic vertebrae prosthesis according to an embodiment of the present invention.
Figure 2:
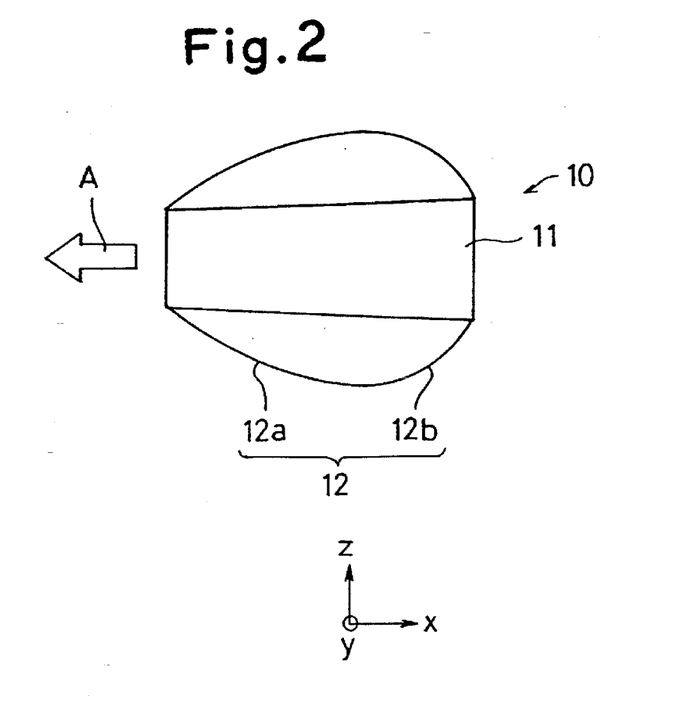
FIG. 2 is a front elevational view of FIG. 1.
Figure 3:
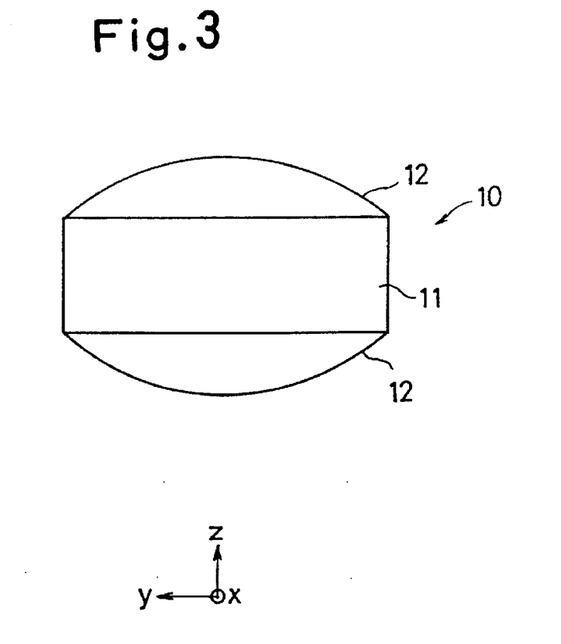
FIG. 3 is a right side elevational view of FIG. 1.

FIGS. 1 through 3 show a ceramic vertebrae prosthesis 10 according to the present invention by way of example. The ceramic vertebrae prosthesis 10 is substantially rectangular in plan view corresponding to the cross sectional shape of the vertebra body (cervical vertebrae or thoracolumber vertebrae). The ceramic prosthesis 10 is has a symmetrical shape with respect to the center axis (median plane) in the vertical direction Z. The ceramic prosthesis 10 is provided with a center portion 11 of wedge-shape which is provided on the upper and lower surfaces thereof with curved contact surfaces 12 which are in the form of a convex surface.

The wedge-shape center portion 11 has a width which gradually decreases toward the front end thereof, in a section in a direction parallel with the direction "A" (i.e., z-x plane) of insertion of the ceramic prosthes is between the vertebra bodies, as can be seen in FIG. 2.

In a section in a direction parallel with the insertion direction "A" (i.e., z-x plane), the contact surfaces 12 are each provided with a front small curvature surface portion 12a (having a large radius of curvature) and a rear large curvature surface portion 12b (having a small radius of curvature) in combination. The curved surface in each cross section in z-y plane perpendicular to the insertion direction "A" is comprised of a curved to surface having one curvature as shown in FIG. 3.

Figure 4:
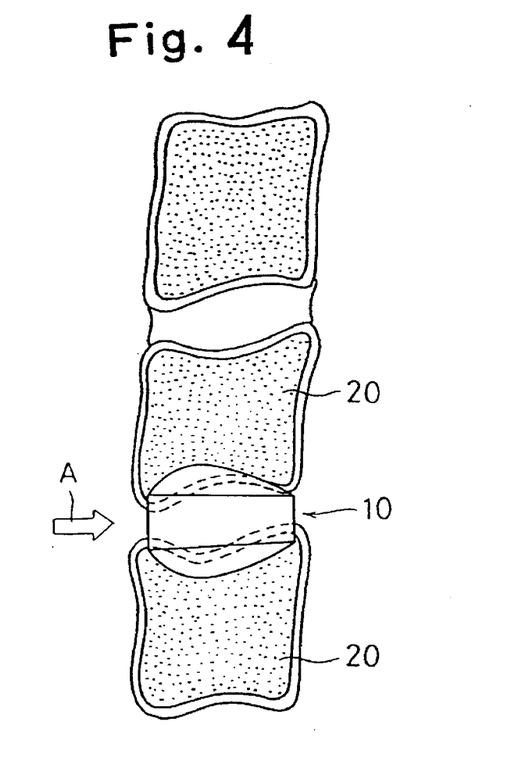
FIG. 4 is a schematic view of a vertebrae prosthesis shown in FIGS. 1 through 3, inserted between vertebra bodies.
Figure 5:
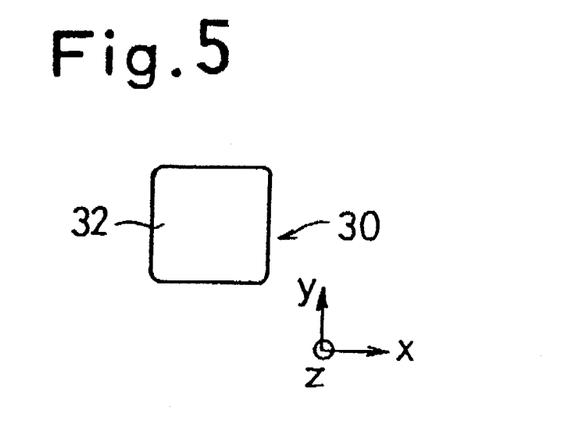
FIG. 5 is a cross sectional plan view of a ceramic cervical vertebrae prosthesis according to an embodiment of the present invention.
Figure 6:
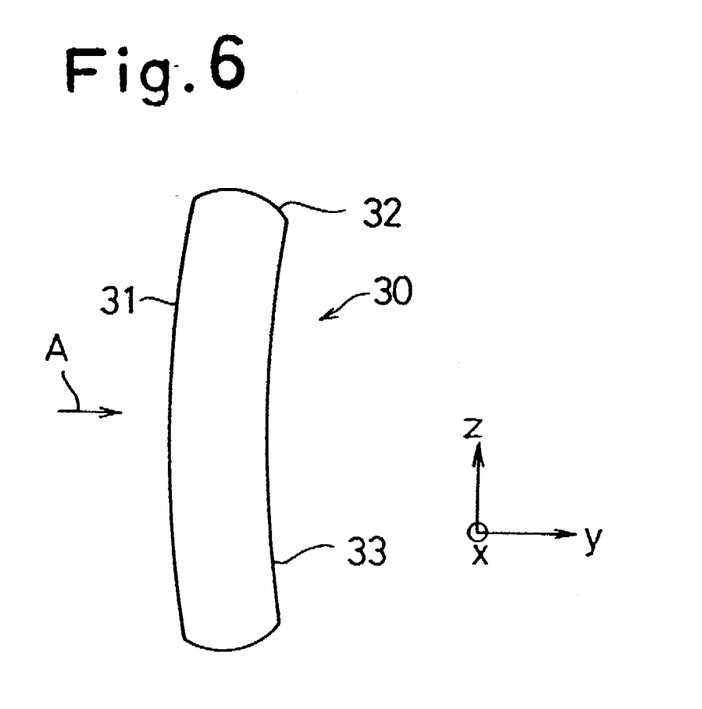
FIG. 6 is a front side elevational view of FIG. 5.
Figure 7:
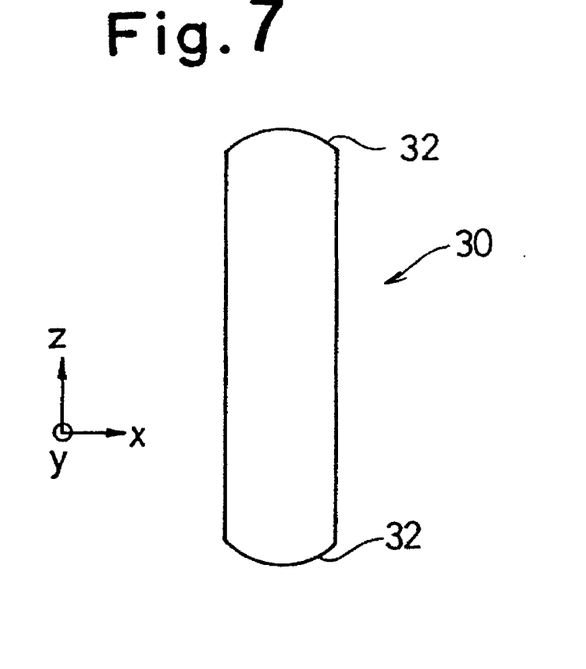
FIG. 7 is a left side elevational view of FIG. 5.
Figure 8:
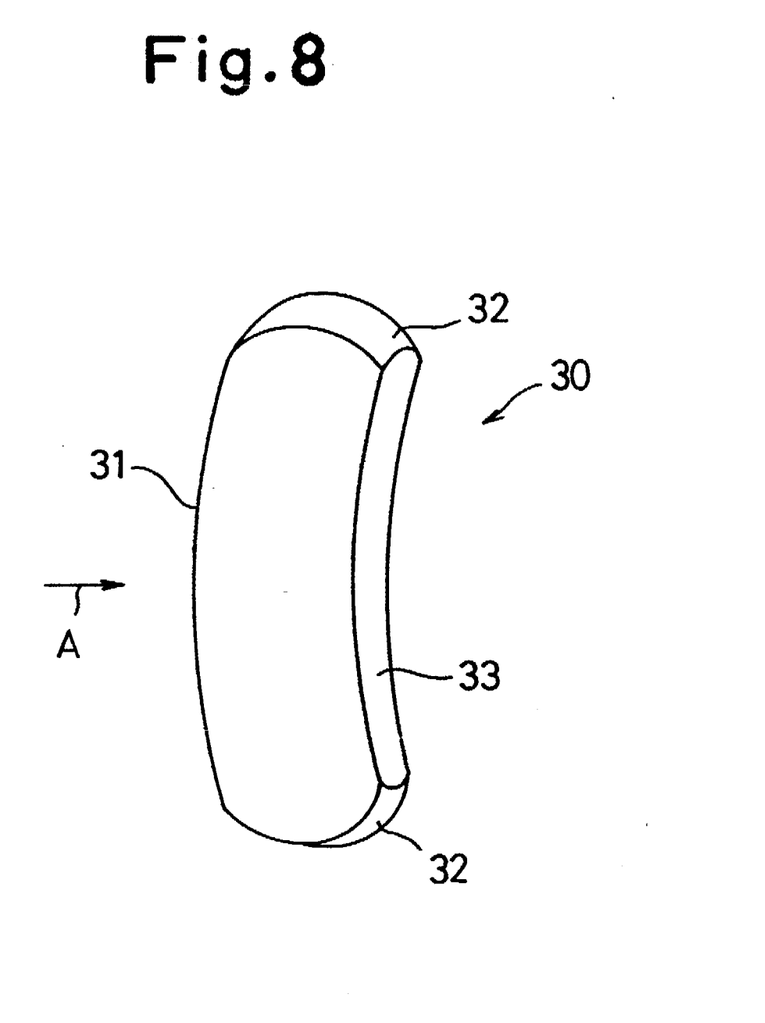
FIG. 8 is a perspective view of FIG. 5.

The ceramic prosthesis 10 as constructed above is inserted between the vertebra bodies 20 with the front small curvature surface portion 12a being the leading end, as can be seen in FIG. 4. Since the small curvature surface portion 12a has a curvature smaller (radius of curvature larger) than the large curvature surface portion 12b, and the wedge-shape portion 11 reduces the thickness thereof at the front end, the ceramic prosthesis 10 can be inserted between the vertebra bodies 20 while expanding the space defined between the vertebra bodies, due to the wedge effect thereof as a whole. When the insertion is completed, the contact surfaces 12 which are in the form of a convex surface consisting of the small curvature surface portion 12a and the large curvature surface portion 12b substantially uniformly distribute or disperse the compression stress exerted by the vertebra bodies 20, and no bone resorption takes place, so that the ceramic prosthesis can be stably held between the vertebra bodies 20. Moreover, the amount of the vertebra bodies 20 to be cut-away can be as small as possible, since the convex surface 12 correspond to the surfaces of the associated vertebra bodies 20 that are macroscopically concave surfaces.

In the illustrated embodiment, although the central portion 11 is in the form of a wedge which contributes, together with the convex contact surfaces 12, to an easy insertion of the ceramic prosthesis, as mentioned above, the central portion 11 may be in the form of a parallel-sided plate. Moreover, in the illustrated embodiment, the vertebrae prosthesis 10 is of a symmetrical shape with respect to the center axis in the vertical direction, and accordingly, the prosthesis can be inserted with either side (upper or lower side in FIGS. 2 and 3) located up. Alternatively, the ceramic vertebrae prosthesis 10 can be of an asymmetrical shape.

The following discussion will be adressed to examples of a production process of the ceramic vertebrae prosthesis 10 according to the present invention.

EXAMPLE 1

A hydroxyapatite slurry was prepared by a wet composition process. The slurry thus obtained was dried by a rotary drum type drier produced by Nishimura Tekkou Seisakusho Co. Ltd., to obtain a hydroxyapatite powder. The powder was calcined at 800° C. in an electric furnace for three hours for an easy handling thereof.

The calcined powder was pressed by a metal press to obtain a green compact in the form of a cylinder whose diameter and length were 35 mm and 35 mm, respectively. The green compact thus obtained was pressed at a hydraulic pressure of 1 ton/cm² by a static hydraulic press to obtain a cylindrical green compact having a mechanical strength strong enough to machine the same. The cylindrical green compact thus obtained was machined by an NC milling machine to produce different sizes of products whose shape is as shown in FIGS. 1 through 3, taking into account a contraction of the green compact caused during a heating process thereof. The products were then heated at 1100° C. in an electric furnace for two hours to obtain different sizes of vertebrae prostheses. The vertebrae prostheses were implanted in patients suffering from an intervertebral disk hernia or the like by the forward adhesion process. As a result, good results were obtained.

EXAMPLE 2

A hydroxyapatite slurry which was prepared by a wet composition process was dried by a rotary drum type drier produced by Nishimura Tekkou Seisakusho Co. Ltd., to obtain a hydroxyapatite powder. The powder was calcined at 800° C. in an electric furnace for three hours for an easy handling thereof.

100 g of albumen albumin was added to and gradually mixed with 200 g of the calcined powder by a dry type ball mill. Thereafter, 500 g of water was added to the mixed powder and foamed for 15 minutes by a hand mixer. Thereafter, the foamed mixture was transferred onto a glass Petri dish having 20 cm diameter and 5 cm depth, and dried at 80° for 24 hours in a drier to obtain a dried porous body. The porous body was cut into parallelepiped shapes and machined by an NC lathe and milling machine to produce different sizes of products whose shape is as shown in FIGS. 1 through 3, taking into account a contraction thereof caused during a burning process thereof. The products were then heated at 1200° C. for three hours in an electric furnace to obtain different sizes of vertebrae prostheses. The vertebrae prostheses were implanted in patients suffering from an intervertebral disk hernia or the like by the forward adhesion process. As a result, good results were obtained.

FIGS. 5 through 9 show a ceramic cervical vertebrae prosthesiac 30 for multiple vertebra bodies according to the present invention, by way of example.

The ceramic cervical vertebrae prosthesis 30 is in the form of an arch corresponding to the shape of the cervical vertebrae, so that when the prosthesis 30 is implanted and adhered, the surface of the prosthesis 30 corresponding to the front surface of the cervical vertebrae is made of a convex surface 31. The upper and lower surfaces of the prosthesis 30, that are brought into contact with the upper and lower vertebra bodies 20, are formed as convex surfaces 32.

Note that the radius of curvature of the front surface 31 of the prosthesis 30 corresponding to the front surface of the cervical vertebrae is not necessarily identical to and can be different from the radius of curvature of the rear surface 33 of the prosthesis 30 opposite to the front surface 31. For instance, if the radius of curvature of the convex front surface 31 of the prosthesis 30 is larger than the radius of curvature of the concave rear surface 33 thereof, the prosthesis 30 can be more easily inserted into a cavity formed when a plurality of vertebra bodies have been resected. In the illustrated embodiment, the radii of curvature of the convex surface 31 and concave surface 33 are 160 mm and 150 mm, respectively.

Figure 9:
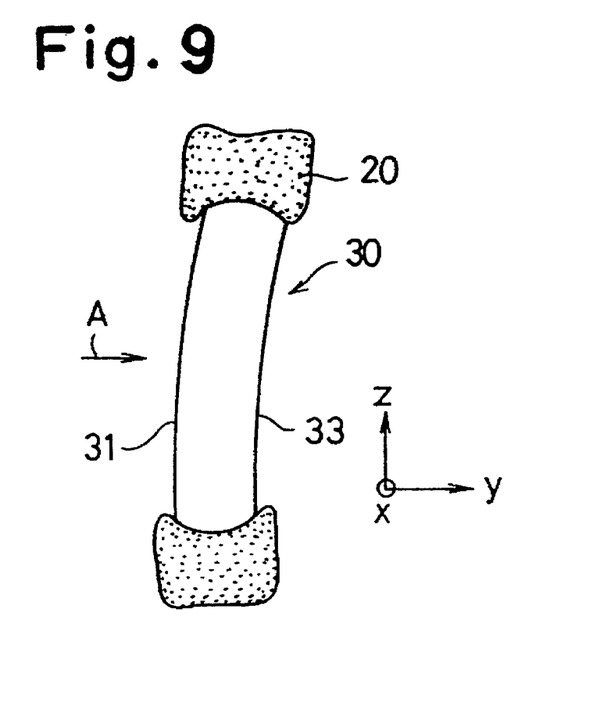
FIG. 9 is a schematic view of a ceramic cervical vertebrae prosthesis shown in FIGS. 5 through 8, inserted between vertebra bodies.

When the ceramic cervical vertebrae prosthesis 30 is inserted, the convex front surface 31 is a leading end, as shown in FIG. 9. Consequently, the cervical vertebrae prosthesis 30 has a natural curve corresponding to the cervical vertebrae. When the insertion of the prosthesis 30 is completed, the convex contact surfaces 32 that come into contact with the vertebra bodies 20 substantially uniformly distribute or disperse the compression stress from the vertebra bodies 20 due to the convexity thereof, so that the prosthesis 30 can be stably held between the vertebra bodies 20 without a bone resorption. Moreover, the amount of the vertebra bodies 20 to be resected is minimized since the surfaces of the vertebra bodies 20 are microscopically concave surfaces, as mentioned above.

Examples of production process of the ceramic cervical vertebrae prosthesis 30 according to the present invention will be discussed below.

EXAMPLE 3

A powder of tricalcium phosphate marketed by Taiheiyou Kagaku Co. Ltd., was calcined at 800° C. for three hours in an electric furnace. It was identified by an X-ray analizer that the calcined powder had a hydroxyapatite crystal structure. The calcined powder was pressed by a metal press to obtain a green compact in the form of a prism of 25 mm×25 mm×80 mm (height). The green compact thus obtained was pressed at a hydraulic pressure of 1 ton/cm² by a static hydraulic press to obtain a prism-shape of green compact having a mechanical strength strong enough to machine the same. The green compact was then machined by an NC milling undergo machining to produce different sizes of products whose shape is as shown in FIGS. 5 through 9, taking into account a contraction of the green compact caused during a heating process thereof. The products were then heated at 1100° C. for two hours in an electric furnace to obtain different sizes of cervical vertebrae prostheses. The cervical vertebrae prostheses were implanted in patients suffering from an intervertebral disk hernia or the like by the forward adhesion process. As a result, good results were obtained after the lapse of six months.

EXAMPLE 4

50 g of albumen albumin was added to and gradually mixed with 200 g of calcined hydroxyapatite powder obtained by the same process as Example 3, mentioned above, by a dry type ball mill. Thereafter, 500 g of water was added to the mixed powder and foamed for 15 minutes by a hand mixer. Thereafter, the foamed mixture was transferred onto a glass Petri dish having 20 cm diameter and 5 cm depth, and dried at 80° C. for 24 hours in a drier to obtain a dried porous body. The porous body was cut into parallelepiped shapes and machined by an NC milling machine to produce different sizes of products whose shape is as shown in FIGS. 5 through 9, taking into account a contraction thereof caused during a heating process thereof. The products were then heated at 1200° C. for three hours in an electric furnace to obtain different sizes of cervical vertebrae prostheses. The cervical vertebrae prostheses were implanted in patients suffering from an intervertebral disk hernia or the like by the forward adhesion process. As a result, good results were obtained after the lapse of seven months.

As can be seen from the above discussion, according to the present invention, a vertebrae prosthesis having an increased resistance to the compression stress can be obtained, wherein no bone resorption of the prosthesis occurs; the amount of the bone of the vertebra body to be resected during the surgical operation can be minimized; the vertebrae prosthesis can be easily inserted between the vertebra bodies; and, the vertebrae prosthesis can be stably held between the vertebra bodies.

Furthermore, according to the present invention, a cervical vertebrae prosthesis for a multiple vertebra bodies can be advantageously implanted in a cavity by a forward adhesion process after a plurality of vertebra bodies are removed. In the cervical vertebrae prosthesis, the compression stress exerted by the associated upper and lower vertebra bodies can be dispersed or uniformly distributed, thus resulting in an increased resistance of the prosthesis to the compression stress. In addition to the foregoing, in the cervical vertebrae prosthesis according to the present invention, no bone resorption takes place; the amount of the bone of the vertebra body to be resected during the surgical operation can be minimized; the cervical vertebrae prosthesis can be easily inserted between the vertebra bodies; the vertebrae prosthesis can be stably held between the vertebra bodies for long period; the prosthesis serves as a morphologically natural substitute, so that an operator or a patient can be remitted from burden or physical load.

We claim:

1. A ceramic vertebra prosthesis to be inserted in a cavity defined between upper and lower vertebra bodies with a removed intervertebral disk or disks, said vertebra prosthesis comprising a ceramic having a porosity of 20 to 55%, wherein the vertebra prosthesis is provided with upper and lower convex contact surfaces that are adapted to come into contact with upper and lower vertebra bodies, each of said upper and lower convex contact surfaces comprises a curved surface whose curvature in a section in a direction perpendicular to a direction of insertion of said vertebra prosthesis into the cavity between the upper and lower vertebra bodies is different than in a direction parallel to the direction of insertion of the vertebra prosthesis;

wherein said prosthesis comprises calcium phosphate ceramic;

wherein a width of said prosthesis decreases in a direction toward an insertion end of said prosthesis; and wherein said width of said prosthesis is greatest at a point disposed between a center and an end opposite said insertion end of said prosthesis.

2. The ceramic vertebra prosthesis according to claim 1, wherein of a radius of curvature of a front curved surface is larger than a radius of curvature of a rear curved surface of said vertebra prosthesis, as viewed in a direction toward an insertion end.

3. A ceramic cervical vertebra prosthesis for multiple vertebra bodies to be inserted in a cavity formed by resecting a plurality of continuous cervical vertebrae, said vertebra prosthesis comprising:

a ceramic having a porosity of 30 to 45%, wherein the vertebra prosthesis is provided with an outwardly arched front surface corresponding to front surfaces of the removed vertebra bodies and upper and lower convex contact surfaces that are adapted to come into contact with the corresponding upper and lower vertebra bodies; and wherein a contour of said outwardly arched front surface protrudes outwardly with respect to a plane defined by a direction of insertion of said vertebra prosthesis and an axis of alignment of the plurality of continuous cervical vertebrae prior to resection.

4. The ceramic cervical vertebra prosthesis according to claim 3, wherein said prosthesis comprises calcium phosphate ceramic.

5. The ceramic cervical vertebra prosthesis according to claim 3, wherein a radius of curvature of said outwardly arched front surface is different than a radius of curvature of a rear surface of said prosthesis.

6. The ceramic cervical vertebra prosthesis according to claim 5, wherein said radius of curvature of said outwardly arched front surface is between 100 mm and 200 mm.

7. A ceramic vertebra prosthesis adapted to be inserted in a cavity defined between upper and lower vertebra bodies upon removal of an intervertebral disk or disks, said vertebra prosthesis comprising a ceramic having a porosity of 20 to 55%, wherein the vertebra prosthesis is provided with upper and lower convex contact surfaces that are adapted to come into contact with upper and lower vertebra bodies, each of said upper and lower convex contact surfaces comprising a curved surface whose curvature in a section in a direction perpendicular to a direction of insertion of said vertebra prosthesis into the cavity between the upper and lower vertebra bodies is different than in a direction parallel to the direction of insertion of the vertebra prosthesis; and wherein a width of said prosthesis is greatest at a point disposed between a center and an end opposite of an insertion end of said prosthesis.

8. The ceramic vertebra prosthesis according to claim 7, wherein said prosthesis comprises calcium phosphate ceramic.

9. The ceramic vertebra prosthesis according to claim 7, wherein of a radius of curvature of a front curved surface is larger than a radius of curvature of a rear curved surface of said vertebra prosthesis, as viewed in a direction toward an insertion end.

10. The ceramic vertebra prosthesis according to claim 7, wherein said prosthesis comprises hydroxyapatite.

11. A cervical vertebra prosthesis for multiple cervical bodies to be inserted in a cavity formed by resecting a plurality of continuous cervical bodies, said vertebra prosthesis comprising:

a substantially rigid body having a length adapted to replace a cavity formed by resecting at least one cervical vertebra and two cervical disks adjacent thereto, said substantially rigid body provided with an outwardly arched anterior surface corresponding to the anterior contour of a portion of the cervical curve defined by anterior surfaces of the removed cervical vertebra body or bodies and cervical disks.

12. The cervical vertebra prosthesis according to claim 11, wherein said substantially rigid body of said prosthesis comprises a superior convex contact surface and an inferior convex contact surface, wherein said convex contact surfaces are adapted to come into contact with corresponding upper and lower vertebra bodies.

13. The cervical vertebra prosthesis according to claim 11, wherein said substantially rigid body of said prosthesis comprises an inwardly arched posterior surface.

14. The cervical vertebra prosthesis according to claim 13, wherein said inwardly arched posterior surface comprises a radius of curvature different from a radius of curvature of said outwardly arched anterior surface.

15. The cervical vertebra prosthesis according to claim 11, wherein said prosthesis comprises ceramic having a porosity of 30 to 45%.

16. The cervical vertebra prosthesis according to claim 11, wherein said prosthesis comprises calcium phosphate ceramic.

17. The cervical vertebra prosthesis according to claim 11, wherein said prosthesis comprises hydroxyapatite.

18. A prosthesis adapted to be inserted in a cavity defined by removal of an intervertebral disk, said prosthesis comprising:

a body having convex superior and inferior contact surfaces adapted to come into contact with upper and lower vertebra bodies, each of said upper and lower convex contact surfaces comprising a curved surface whose curvature in a frontal section of said prosthesis is different than in a sagittal section of said prosthesis; and wherein a width of said sagittal section of said prosthesis is greatest along a line posterior to a center of said sagittal section.

19. The prosthesis according to claim 18, wherein said body comprises a ceramic body.

20. The prosthesis according to claim 18,
wherein a width of a frontal section of said prosthesis is greatest at a center of said frontal section.

21. The prosthesis according to claim 19, wherein said ceramic body comprises a ceramic having a porosity of 20 to 55%.

* * * * *